United States Patent [19]

Tamir et al.

[11] Patent Number: 4,482,567
[45] Date of Patent: Nov. 13, 1984

[54] N-HEXANOYL TO N-HEPTADECANOYL 5-HYDROXY TRYPTOPHAN-5-HYDROXYTRYPTO-PHANAMIDES AND USE AS ANALGESICS

[75] Inventors: Hadassah Tamir, Teaneck, N.J.; Stephen E. Karpiak, New York, N.Y.; Meir Wilchek, Rehovoth, Israel

[73] Assignees: Research Foundation for Mental Hygiene, Inc., New York, N.Y.; Yeda Research and Development Co. Ltd., Rehovoth, Israel

[21] Appl. No.: 433,283

[22] Filed: Oct. 7, 1982

[51] Int. Cl.$^3$ .................. A61K 31/405; C07D 401/12
[52] U.S. Cl. ................................. 424/274; 548/455; 260/112.5 R
[58] Field of Search ............................ 548/495, 455; 260/112.5 R; 424/274

[56] References Cited

U.S. PATENT DOCUMENTS 2,701,800  2/1955  Britton et al. ................ 548/495
3,330,857  7/1967  Hess et al. ................... 548/455

OTHER PUBLICATIONS

Tamir et al. (I), J. Neurochem., 32, 593–595, (1979).
Tamir et al. (II), Life Sciences, vol. 25, pp. 655–664, (1979).
Terashima et al., Tetrahedron, vol. 29, pp. 1487–1496, 1973.

Primary Examiner—Glennon H. Hollrah
Assistant Examiner—D. B. Springer
Attorney, Agent, or Firm—Morgan, Finnegan, Pine, Foley & Lee

[57] ABSTRACT

Analgesia-effecting 5-hydroxytryptophan derivatives are disclosed of the formulae:

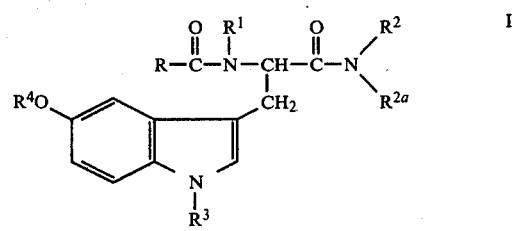

and

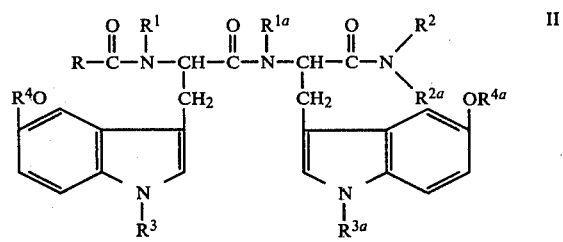

wherein R is selected from the group consisting of $C_2$–$C_{16}$ alkyl, $C_3$–$C_8$ cycloalkyl, $C_2$–$C_{16}$ alkenyl, $C_2$–$C_{16}$ alkynyl, aryl containing up to 14 carbon atoms, and arylalkyl containing up to 20 carbon atoms;

$R^1$ and $R^{1a}$ are each H or methyl;
$R^2$ and $R^{2a}$ are each H or R, as defined above;
$R^3$ and $R^{3a}$ are each H or alkyl containing from 1 to 4 carbons;
$R^4$ and $R^{4a}$ are each H or alkyl containing from 1 to 4 carbons;
and their non-toxic, pharmacologically acceptable acid addition salts.

12 Claims, No Drawings

N-HEXANOYL TO N-HEPTADECANOYL 5-HYDROXY TRYPTOPHAN-5-HYDROXYTRYPTOPHANAMIDES AND USE AS ANALGESICS

BACKGROUND OF THE INVENTION

1. Field of the Invention

This invention relates in general to 5-hydroxytryptophan derivatives and their use as analgesic compounds. More particularly, it relates to N-substituted derivatives of 5-hydroxytryptophan and dimers thereof.

2. Description of the Prior Art

5-Hydroxytryptophyl peptides of similar structure are described in two literature publications: H. Tamir and M. Wilchek, J. Neurochem 32, 593–598 (1979) and H. Tamir et al, Life Sciences, Vol. 25, pp 655–664 (1979).

In the first publication, the peptides 5HTP-5HTP amide; N-acetyl-5HTP-5HTP amide and the derivative 5HTP methyl ester are described and their effect on the binding of serotonin to serotonin-binding protein (SBP) is disclosed.

The second reference describes the analgesic effects of N-acetyl-5HTP-5HTP amide, one of the compounds recited in the first publication.

As is evident by visual inspection, the compounds disclosed and claimed herein differ structurally from the N-acetyl derivative recited above in that inter alia, substituent R of compounds represented by formula I or II has a minimum carbon chain of two carbons, and preferably at least three. Functionally, this difference provides unexpectedly, significantly different properties. The N-acetyl derivative, only when injected intraventricularly, affects pain threshold, but it does not pass through the blood-brain barrier. It has no effect when injected intraperitoneally (I.P.) even at very high doses.

In contrast, the compounds disclosed and claimed herein successfully reach the brain by passing through the blood-brain barrier. As a result, the instant compounds significantly and lastingly raise the pain threshold of pain without affecting activity when administered intraperitoneally.

Moreover, the instant compounds are believed to be non-addicting, have no cross-tolerance with morphine and appear to have little or no toxic effect.

Because of these unusual characteristics, the compounds of this invention fulfill a real need in this art and the industry in general.

SUMMARY OF THE INVENTION

In accordance with this invention, there is disclosed and claimed 5-hydroxytryptophan derivatives having the formulae:

$$\text{R}-\underset{\text{O}}{\overset{\text{O}}{\text{C}}}-\underset{\text{R}^1}{\text{N}}-\underset{\underset{\text{indole(R}^4\text{O, R}^3\text{)}}{|}}{\text{CH}}-\underset{\text{O}}{\overset{\text{O}}{\text{C}}}-\text{N}\underset{\text{R}^{2a}}{\overset{\text{R}^2}{<}} \quad \text{I}$$

and $$\text{R}-\underset{\text{O}}{\overset{\text{O}}{\text{C}}}-\underset{\text{R}^1}{\text{N}}-\underset{\underset{\text{indole(R}^4\text{O, R}^3\text{)}}{|}}{\text{CH}}-\underset{\text{O}}{\overset{\text{O}}{\text{C}}}-\underset{\text{R}^{1a}}{\text{N}}-\underset{\underset{\text{indole(R}^{4a}\text{O, R}^{3a}\text{)}}{|}}{\text{CH}}-\underset{\text{O}}{\overset{\text{O}}{\text{C}}}-\text{N}\underset{\text{R}^{2a}}{\overset{\text{R}^2}{<}} \quad \text{II}$$

wherein R is selected from the group consisting of $C_2$–$C_{16}$ alkyl, $C_3$–$C_8$ cycloalkyl, $C_2$–$C_{16}$ alkenyl, $C_2$–$C_{16}$ alkynyl, aryl containing up to 14 carbon atoms, and arylalkyl containing up to 20 carbon atoms;

$R^1$ and $R^{1a}$ are each H or methyl;

$R^2$ and $R^{2a}$ are each H or R, as defined above;

$R^3$ and $R^{3a}$ are each H or alkyl containing from 1 to 4 carbons;

$R^4$ and $R^{4a}$ are each H or alkyl containing from 1 to 4 carbons;

and their non-toxic, pharmacologically acceptable acid addition salts.

Particularly preferred compounds are those of formula I in which R is alkyl of 3 to 6 carbon atoms, such as n-pentyl, n-propyl, n-butyl and n-hexyl, $R^1$ is hydrogen, $R^2$ and $R^{2a}$ are each hydrogen, $R^3$ is hydrogen and $R^4$ is hydrogen.

Similarly, preferred compounds comprise those of formula II wherein R is alkyl of 3 to 6 carbon atoms, e.g. n-pentyl, $R^1$ and $R^{1a}$ are each hydrogen, $R^2$ and $R^{2a}$ are each hydrogen, $R^3$ and $R^{3a}$ are each hydrogen and $R^4$ and $R^{4a}$ are both hydrogen.

Analgesic compositions which contain the compounds disclosed herein are within the purview of this invention as well as their use in raising the pain threshold in warm-blood animals.

DETAILED DESCRIPTION OF THE INVENTION

The novel compounds of this invention are derivatives of 5-hydroxytryptophan. More particularly, they are N-hydrocarbonoxy derivatives of 5-hydroxytryptophan (5HTP) amide wherein the amide nitrogen may optionally contain other substituents.

The compounds embraced by formula I as shown hereinbelow

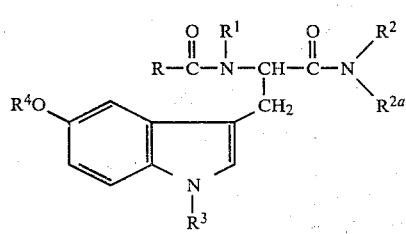

may be reviewed as monomeric, i.e., contain one 5-HTP nucleus, wherein those of formula II, reproduced hereinbelow

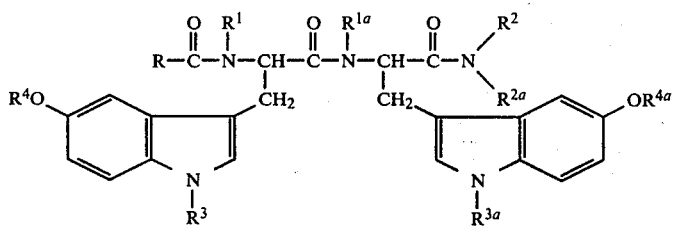

are dimeric, i.e., derived from two 5-HTP nuclei.

Theoretically, the molecule can also be a trimer, a tetramer or more, and such structures are contemplated herein in the sense that the active species is believed to be the monomer or dimer or mixtures thereof. Thus, if the repeating unit is extended to include additional 5-HTP units, on breakdown in the animal body, the resulting active species is believed to be as shown in formulas I or II.

The compounds of this invention can be prepared in the following general manner:

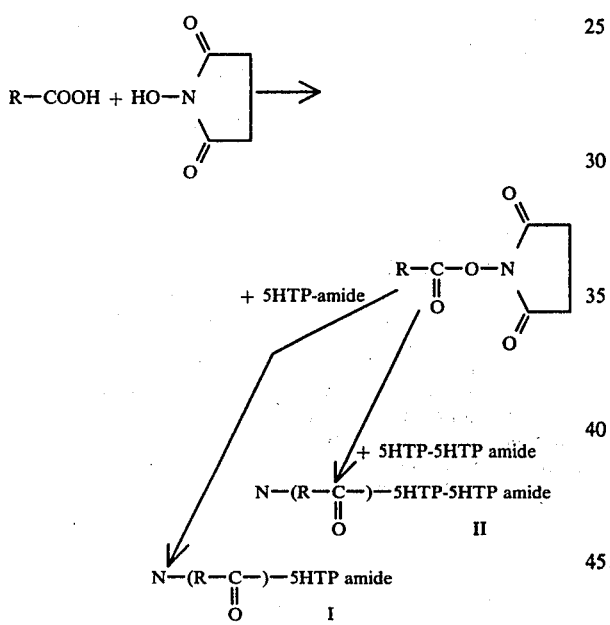

The amide can be converted to the corresponding mono- or di-substituted amide by conventional means.

Furthermore, acid-addition salts are obtained similarly by art-accepted procedures.

For therapeutic application the compounds of the present invention may be administered orally, parenterally or rectally as active ingredients in dosage unit compositions, that is, in compositions consisting essentially of an inert, physiologically compatible carrier having distributed therein one dosage unit of the active ingredient. One dosage unit of the compounds of this invention is from 0.5 to 50 mg/kg.

The compounds of this invention were found to be highly effective analgesics in that they readily penetrate the blood-brain barrier and by a mechanism, not completely understood at this time, elevate the pain threshold of the subject being treated.

EXAMPLE I

Hexanoyl-5-hydroxy-L-Trp-5-hydroxy-L-Trp amide.

Hexanoic acid (1 m mol), dissolved in dioxane, was combined with N-hydroxysuccinimide (1.1 m mol). To this reaction mixture was added dicyclohexylcarbodiimide (1.1 m mol) and the resulting mixture allowed to stand for up to 24 hours at room temperature. The mixture was then filtered and the filtrate solution evaporated to dryness.

5-Hydroxy-L-Trp-5-hydroxy-L-Trp amide (1 m mol) was dissolved in 0.2M NaOH (15 ml) and then combined with the dried intermediate (1 m mol) obtained in the preceding step. The reaction mixture was allowed to stand for 1 hr. at room temperature, after which, the product was obtained by recovering the precipitate formed by the addition of HCl.

EXAMPLE II

The procedure of Example I is repeated wherein, instead of hexanoic acid, the following reagents are used in stoichiometric equivalent amounts to provide corresponding products:
butanoic acid
octanoic acid
dodecanoic acid
hexadecyloic acid
1-butenoic acid
1-hexenoic acid
1-butynoic acid
benzoic acid
benzyloic acid
propionic acid

EXAMPLE III

The procedure of Example I is duplicated except that 5HTP amide is used, in equivalent amounts, instead of 5HTP-5HTP amide to give the corresponding product. Similarly, when this procedure is repeated employing the acids recited in Example II, the corresponding compounds are obtained.

EXAMPLE IV

The procedure of Example I is repeated except that instead of 5HTP-5HTP amide, stoichiometric equivalent amounts of the N,N-dimethyl amide of 5HTP-5HTP is used, to give the corresponding product.

EXAMPLE V

The present study examines the effectiveness of intraventricular injections of small amounts of N-hexanoyl-5HTP-5HTP amide to alter reflex pain thresholds as measured by the flinch-jump test.

Pain Threshold Determination

Flinch-Jump Test

Male Sprague-Dawley rats (275–300 g) were tested in a 12" by 10" plexiglass box with a floor consisting of 8 grid bars through which scrambled electric foot shocks were delivered. Using an ascending method of limits, the flinch response was defined in mA as the lowest intensity that elicited withdrawal of a single paw from the grids. The jump response was defined as the lowest of two consecutive intensities that elicited simultaneous withdrawal of both hindpaws from the grids. Each test of 10 daily trials began with the animal receiving a 500 m sec foot shock at a current intensity of 0.05 mA, followed by 0.05 mA increments every 10 seconds. A trial was completed when the jump response was elicited. Daily flinch and jump thresholds were expressed as a mean of these 10 trials. The third of three testing days served as baseline. Since flinch thresholds were almost perfectly correlated with jump thresholds, only the jump threshold data were analyzed. All baselines were adjusted to be equal to zero for data analysis. Doses of 1, 5, 10, 25 and 50 mg/kg were tested.

Results

Effect of Hexanoyl-5HTP-5HTP Amide on Pain Threshold

Following determination of baseline flinch-jump thresholds, rats received an intraperitoneal injection of either the dipeptide hexanoyl-5HTP-5HTP amide (n=10) or the saline vehicle (n=9). Fifteen to twenty minutes after the injection, rats were tested for flinch-jump thresholds. Further post-injection flinch-jump thresholds were determined in like manner at varying time intervals for up to 5 hrs. and then at 24 hrs. Injection of the dipeptide at 10–50 mg/kg produced significant (p<0.01) elevations in flinch-jump thresholds. The onset of the analgesic response occurred at <1 hr. after the injection and lasted for as long as 5 hrs. The analgesic property of the dipeptide suggested that it may interact with opiate receptors. We have therefore tested the capacity of naloxone to reverse this analgesic effect. Injection and testing procedures were identical to those of the previous experiment. The rats were tested for flinch-jump thresholds 2.5 hrs. following I.P. injection of either dipeptide or saline. Immediately thereafter, naloxone (1 mg/kg i.p.) was administered and flinch-jump thresholds were determined. Naloxone reversed the effect within a short time. Complete reversal could be demonstrated within 15 minutes after injection.

It should be understood by those skilled in the art that various modifications may be made in the present invention without departing from the spirit and scope thereof as described in the specification and defined in the appended claims.

What is claimed is:

1. A compound selected from the group consisting of 5-hydroxytryptophan derivatives of the formula:

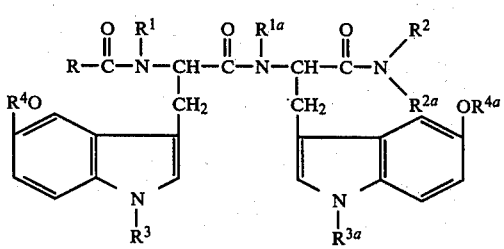

wherein R is selected from the group consisting of $C_5$–$C_{16}$ alkyl;

$R^1$ and $R^{1a}$ are each H or methyl;

$R^2$ and $R^{2a}$ are each H or R, as defined above;

$R^3$ and $R^{3a}$ are each H or alkyl having from 1 to 4 carbons;

$R^4$ and $R^{4a}$ are each H or alkyl having from 1 to 4 carbons;

and their non-toxic, pharmacologically acceptable acid addition salts.

2. Compounds of claim 1 wherein R is alkyl of 5 or 6 carbons, $R^1$ and $R^{1a}$ are each H, $R^2$ and $R^{2a}$ are each H, $R^3$ and $R^{3a}$ are each H, and $R^4$ and $R^{4a}$ are each H.

3. A compound of claim 2 wherein R is n-pentyl.

4. A compound of claim 2 wherein R is n-hexyl.

5. An analgesic composition consisting essentially of an inert, physiologically compatible carrier and an analgesic-effective amount of a compound selected from the group consisting of 5-hydroxytryptophan derivatives of the formula:

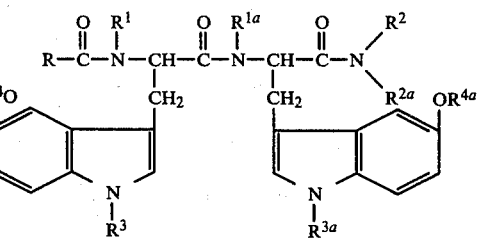

wherein R is selected from the group consisting of $C_5$–$C_{16}$ alkyl;

$R^1$ and $R^{1a}$ are each H or methyl;

$R^2$ and $R^{2a}$ are each H or R, as defined above;

$R^3$ and $R^{3a}$ are each H or alkyl having from 1 to 4 carbons;

$R^4$ and $R^{4a}$ are each H or alkyl having from 1 to 4 carbons;

and their non-toxic, pharmacologically acceptable acid addition salts.

6. Compounds of claim 5 wherein R is alkyl or 5 or 6 carbons, $R^1$ and $R^{1a}$ are each H, $R^2$ and $R^{2a}$ are each H, $R^3$ and $R^{3a}$ are each H, and $R^4$ and $R^{4a}$ are each H.

7. A compound of claim 6 wherein R is n-pentyl.

8. A compound of claim 6 wherein R is n-hexyl.

9. A method of raising the pain threshold in warm-blooded animals which comprises administering to said animals an effective amount of a compound selected from the group consisting of 5-hydroxytryptophan derivatives of the formula:

wherein R is selected from the group consisting of $C_5$–$C_{16}$ alkyl;

$R^1$ and $R^{1a}$ are each H or methyl;

$R^2$ and $R^{2a}$ are each H or R, as defined above;

$R^3$ and $R^{3a}$ are each H or alkyl having from 1 to 4 carbons;

$R^4$ and $R^{4a}$ are each H or alkyl having from 1 to 4 carbons;

and their non-toxic, pharmacologically acceptable acid addition salts.

10. The method of claim 9 wherein R is alkyl of 5 or 6 carbons, $R^1$ and $R^{1a}$ are each H, $R^2$ and $R^{2a}$ are each H, $R^3$ and $R^{3a}$ are each H, and $R^4$ and $R^{4a}$ are each H.

11. The method of claim 10 wherein R is n-pentyl.

12. The method of claim 10 wherein R is n-hexyl.

* * * * *